United States Patent
Wang et al.

(10) Patent No.: US 12,059,423 B2
(45) Date of Patent: Aug. 13, 2024

(54) MELOXICAM COMPOSITION, PHARMACEUTICAL PREPARATION AND PREPARATION METHOD AND USE THEREOF

(71) Applicant: NANJING DELOVA BIOTECH CO. LTD., Jiangsu (CN)

(72) Inventors: Qingsong Wang, Jiangsu (CN); Wenliang Zhou, Jiangsu (CN); Qu Wu, Jiangsu (CN); Limin Zou, Jiangsu (CN)

(73) Assignee: NANJING DELOVA BIOTECH CO., LTD., Jiangsu (CN)

( * ) Notice: Subject to any disclaimer, the term of this patent is extended or adjusted under 35 U.S.C. 154(b) by 436 days.

(21) Appl. No.: 17/044,767

(22) PCT Filed: May 10, 2019

(86) PCT No.: PCT/CN2019/086424
§ 371 (c)(1),
(2) Date: Oct. 1, 2020

(87) PCT Pub. No.: WO2019/214715
PCT Pub. Date: Nov. 14, 2019

(65) Prior Publication Data
US 2021/0106591 A1  Apr. 15, 2021

(30) Foreign Application Priority Data
May 11, 2018 (CN) .......................... 201810450456.6
May 11, 2018 (CN) .......................... 201810451076.4

(51) Int. Cl.
| | | |
|---|---|---|
| *A61K 31/5415* | (2006.01) | |
| *A61K 9/00* | (2006.01) | |
| *A61K 9/08* | (2006.01) | |
| *A61K 47/02* | (2006.01) | |
| *A61K 47/10* | (2017.01) | |
| *A61K 47/12* | (2006.01) | |
| *A61K 47/18* | (2017.01) | |
| *A61K 47/34* | (2017.01) | |

(52) U.S. Cl.
CPC ........ *A61K 31/5415* (2013.01); *A61K 9/0019* (2013.01); *A61K 9/08* (2013.01); *A61K 47/02* (2013.01); *A61K 47/10* (2013.01); *A61K 47/12* (2013.01); *A61K 47/183* (2013.01); *A61K 47/34* (2013.01)

(58) Field of Classification Search
CPC .... A61K 31/5415; A61K 9/0019; A61K 9/08; A61K 47/02; A61K 47/10; A61K 47/12; A61K 47/183; A61K 47/34; A61P 19/02; A61P 19/08; A61P 29/00
See application file for complete search history.

(56) References Cited

U.S. PATENT DOCUMENTS

| | | | |
|---|---|---|---|
| 9,345,665 B2 | 5/2016 | Ryde et al. | |
| 2002/0035107 A1* | 3/2002 | Henke et al. ...... | A61K 31/5415 514/226.5 |
| 2003/0119825 A1 | 6/2003 | Folger et al. | |
| 2005/0245510 A1 | 11/2005 | Friton et al. | |
| 2010/0137292 A1* | 10/2010 | Turp et al. ......... | A61K 31/5415 514/226.5 |
| 2015/0051198 A1 | 2/2015 | Folger et al. | |
| 2017/0157061 A1 | 6/2017 | Cooper et al. | |

FOREIGN PATENT DOCUMENTS

| | | |
|---|---|---|
| CN | 1437472 A | 8/2003 |
| CN | 1493292 A | 5/2004 |
| CN | 1236774 C | 1/2006 |
| CN | 1950090 A | 4/2007 |
| CN | 102908310 A | 2/2013 |
| CN | 103110575 A | 5/2013 |
| CN | 103690480 A | 4/2014 |
| CN | 104825396 A | 8/2015 |
| JP | 2003535902 A | 12/2003 |
| JP | 2005511720 A | 4/2005 |
| JP | 2007534717 A | 11/2007 |
| JP | 2008523024 A | 7/2008 |
| JP | 2011207875 A | 10/2011 |

(Continued)

OTHER PUBLICATIONS

Strickley, Richard, Pharmaceutical Research 2004, vol. 21(2), pp. 201-230 (Year: 2004).*
Cardenas et al., J. Molecular Liquids vol. 211 (2015), pp. 233-238. (Year: 2015).*
European Medicines Agency, Committee for Medicinal Products for Veterinary Use Assessment Report for Recocam (EMEA/V/C/002247) http://www.ema.europa.eu/en/medicines/veterinary/EPAR/recocam#product-information-sectionema.europa.eu/en/medicines/veterinary/EPAR/recocam#product-information-section, Acessed on May 15, 2023, pp. 1-8.
European Patent Office, Extended European Search Report of EP 19800759.3 (U.S. Appl. No. 17/044,767 counterpart application), Jun. 7, 2021.

(Continued)

*Primary Examiner* — Craig D Ricci
*Assistant Examiner* — Janet L Coppins
(74) *Attorney, Agent, or Firm* — NLK Law; Allen Xue

(57) ABSTRACT

The disclosure is related to a meloxicam compositions, pharmaceutical preparations, preparation methods and use thereof. In one aspect of the invention, meloxicam compositions contain meloxicam and cosolvents. The cosolvents are mixed solvents including water and organic solvents. In another aspect of the invention, other compositions contain meloxicam, solvents, and pH regulators. The pH regulators include at least citric acid. The pharmaceutical compositions significantly enhance the solubility of meloxicam in liquid pharmaceutical preparations as well as stability. The meloxicam compositions can be directly used for intravenous injection administration to quickly reach effective therapeutic concentrations for post-operative analgesia.

12 Claims, No Drawings

(56) References Cited

FOREIGN PATENT DOCUMENTS

| JP | 2013507440 A | 3/2013 |
|----|--------------|--------|
| JP | 2013521253 A | 6/2013 |
| WO | 0197813 A2 | 12/2001 |
| WO | 2008062274 A2 | 5/2008 |

OTHER PUBLICATIONS

Rowe, R. C. et al; "Handbook of Pharmaceutical Excipients sixth ed (6)"; United Kingdom: Pharmaceutical Press. Year: 2009; pp. 581-585.
Modhave, Dattatray T. et al.; "Successful characterization of degradation products of drugs using LC-MS tools: Application to piroxicam and meloxicam"; Analytical Methods; vol. 3; Year: 2011; pp. 2864-2872.
Seedher, Neelam et al.; "Solubility Enhancement of Cox-2 Inhibitors Using Various Solvent Systems"; AAPS PharmSciTech; vol. 4, No. 3, Article 33; Year: 2003; pp. 1-9.
Cardenas, Zaira J. et al.: "Solubility and solution thermodynamics of meloxicam in polyethylene glycol 400+ water mixtures"; Journal of Molecular Liquids; vol. 211; Jul. 20, 2015; pp. 233-238.

\* cited by examiner

MELOXICAM COMPOSITION, PHARMACEUTICAL PREPARATION AND PREPARATION METHOD AND USE THEREOF

CROSS-REFERENCE TO RELATED APPLICATIONS

This application is a U.S. national entry of PCT International Application No. PCT/CN2019/086424, filed May 10, 2019, which claims the benefit of and priority of the prior Chinese patent applications: CN 201810450456.6 submitted to China National Intellectual Property Administration on May 11, 2018, which is entitled "Meloxicam composition, pharmaceutical preparation, and preparation method and use thereof"; and CN 201810451076.4 submitted to China National Intellectual Property Administration on May 11, 2018, which is entitled "Meloxicam composition comprising pH regulator, preparation method and use thereof". All of the prior applications are hereby incorporated by reference in their entirety.

TECHNICAL FIELD

The invention belongs to the field of pharmaceutical preparation, specifically relates to a meloxicam composition, pharmaceutical preparation, preparation method and use thereof.

BACKGROUND

Meloxicam (or "MLX") is an enolic nonsteroidal anti-inflammatory drug having a molecular formula of $C_{14}H_{13}N_3O_4S_2$, a molecular weight of 351.40 and a chemical name of 4-hydroxy-2-methyl-N-(5-methyl-2-thiazolyl)-2H-1,2-benzothiazine-3-carboxamide-1,1-dioxide. The compound has the following chemical structural formula:

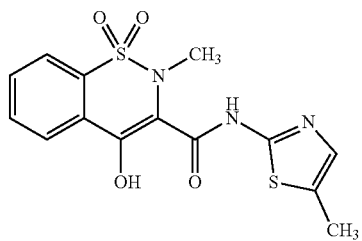 [SMILES: Cc1cnc(NC(=O)C2=C(O)c3ccccc3S(=O)(=O)N2C)s1]

Meloxicam is almost insoluble in water, its solubility in water is only 0.003414 mg/mL at 25° C., and it is slightly soluble in chloroform, acetone and ethanol. Therefore, although a variety of dosage forms of meloxicam have been developed by Boehringer Ingelheim Pharmaceuticals, Iroko Pharmaceuticals, Recro Pharma, etc., increasing the solubility of meloxicam is still a challenging subject in the development of intravenous injections of meloxicam.

For poorly soluble drugs, the physicochemical properties of the drugs can be changed to improve its solubility, such as by converting the drugs into salt forms or changing the crystal forms of the drugs. For example, Ochi et al. used the recrystallization method for converting meloxicam with Tris, arginine, diethanolamine (DEA), or triethanolamine (TEA), etc. into a salt form. Alladi Saritha et al. applied the spherical crystallization method for changing a crystal form of meloxicam into a spherical shape to increase its dissolution rate. However, the methods for forming salts or for changing crystal forms have limitations. For instance, it is required to separate drugs from their salts for the salt-forming methods, and the formation of a crystal is affected by various factors, such as stirring speed, stirring time, temperature and the type of solvent, etc., and limited because of the preparation methods and the stability of salts or crystal forms.

In addition, it is also possible to increase the solubility of poorly soluble drugs from the perspective of formulation, for example, by using mixed solvents, inclusion techniques or new techniques for new dosage forms. Currently, meloxicam has also been studied by the above-mentioned methods both domestic and abroad, but people confront with the problems of complicated preparation processes, excessive use of excipients, and a variety of excipients and organic solvents which are not suitable for intravenous injection administration.

For example, WO2008062274A2 discloses increasing the solubility of meloxicam by using a mixed solvent containing pyrrolidone, ethanol and water, but pyrrolidone is not suitable for intravenous administration. US2010137292A1 discloses solubiliing meloxicam by using a mixed solvent containing meglumine as an organic base, N,N-dimethylacetamide and polyethylene glycol, but N,N-dimethylacetamide is also not suitable for intravenous administration. Furthermore, CN103110575A discloses an ophthalmic preparation containing meloxicam at a concentration of 1 mg/mL prepared by using cyclodextrin as a solubilizer, and adding a stabilizer, a pH regulator, an antibacterial agent and an osmotic pressure regulator. US2017157061A1 discloses that the solubility of meloxicam is also increased by forming nanoparticles prepared with meloxicam and a stabilizer (including polyvinylpyrrolidone, a surfactant, etc.). U.S. Pat. No. 9,345,665B2 discloses a meloxicam nanoparticulate composition containing at least one surfactant and a stabilizer to improve drug loading of meloxicam. Woraphatphadung et al. disclose a chitosan micelle loaded meloxicam to increase the solubility of meloxicam. CN104825396A discloses particles with a particle size of greater than 1 μm by grinding meloxicam with a grinding matrix to improve the dissolution characteristics of the bioactive substance.

However, organic solvents, surfactants, cyclodextrins and other components were used too much in the above-mentioned methods, it is easy to cause safety problems for intravenous injections. Moreover, the preparation processes for new technologies of new dosage forms such as nanoparticles are more complicated, the risk of quality control is high, and there are certain difficulties in the commercial production.

The solubility of meloxicam in pure PEG 400 is 3.763 mg/mL, found by Neelam Seeder et al. If the solubility of meloxicam is up to 1.5 mg/mL, the solvent must be ethanol, propylene glycol, PEG 400, or a mixed solution of PEG 400 and ethanol (PEG 400≥40%), and the solution pH≥9.58. And if the solubility is up to 3.75 mg/mL, the solvent must be ethanol, propylene glycol, PEG 400, or a mixed solution of PEG 400 and ethanol (PEG 400≥80%), and the solution pH≥9.85. Zaira J. Cardenas et al. found that the solubility of meloxicam in PEG 400 aqueous solution is increased with increasing the concentration of PEG 400, and the maximum solubility in pure PEG 400 is 9.2 mg/mL. Dattatray T. Modhave et al. reported that the meloxicam contains an amide bond in its molecule, which may undergo hydrolysis. Patent CN1236774C discloses a formulation containing organic bases, various cosolvents and surfactants, which can only be used for intramuscular injections due to limitations associated with the safety of excipients, and have to be prepared at 90° C., resulting in increasing the risk of degradation products, and harsh production conditions.

In summary, there is an urgent need to develop intravenous injections of meloxicam with improved safety and stability, and convenient preparation technique of formulations.

In another aspect, it is well known that when preparing meloxicam liquid preparations, especially injections, the issue of safety must be considered, for example, increasing the stability of preparations and decreasing the impurity content. However, it is usually a technical problem that perplexes technicians and difficult to be solved. Furthermore, because meloxicam is almost insoluble in water that the solubility in water is only 0.003414 mg/mL at 25° C., and meloxicam is slightly soluble in chloroform, acetone and ethanol, it is generally considered that such solubility properties are unfavorable to improve the stability of liquid-containing preparations. Therefore, under the premise of improving the stability and decreasing the impurity content, if the solubility of meloxicam liquid preparations can be further improved, it is beneficial to extend uses of meloxicam, improve patient compliance, and improve the safety and efficiency of the preparations.

However, for meloxicam injections, the solubility of poorly soluble drugs is usually improved by using mixed solvents or inclusion techniques. Currently, meloxicam has also been studied by the aforementioned methods both domestic and abroad, but people confront with the problems of complicated preparation processes, poor stability, and easily causing safety problems during intravenous injections, which seriously affect the quality control and safety of the injections.

Therefore, it is urgent to develop meloxicam liquid compositions with improved safety and stability, and decreased impurity content, or even with further enhanced solubility and convenient preparation technique of formulations.

SUMMARY OF THE DISCLOSURE

In order to improve the above technical problems, according to an aspect of the invention, the following technical solution is provided: a meloxicam composition containing meloxicam and cosolvent, wherein the cosolvent is a mixed solvent containing water and an organic solvent.

According to an embodiment of the invention, the concentration by volume of the organic solvent in the cosolvent is in the range of 1% to 80%, preferably 5% to 80%, such as 10% to 60%, or 15% to 50%, or 20% to 40%, for example, 15%, 18%, 19%, 20%, 25% or 30%.

According to the invention, the organic solvent is one, two or more selected from the group consisting of ethanol, propylene glycol, butanediol, isopropanol, tetrahydrofurfurol, tetrahydrofuran polyethylene glycol ether, glycerol, dimethylacetamide, polyethylene glycol (also known as PEG, such as polyethylene glycol 300, polyethylene glycol 400, polyethylene glycol 600), etc.; preferably one, two or more selected from the group consisting of ethanol, propylene glycol, butanediol, tetrahydrofurfurol, glycerol, polyethylene glycol 300, polyethylene glycol 400; such as one, two or more selected from the group consisting of ethanol, propylene glycol, polyethylene glycol 300, polyethylene glycol 400; exemplarily, the organic solvent is selected from polyethylene glycol 300 and/or polyethylene glycol 400.

According to the invention, water in the cosolvents can be that suitable for pharmaceutical purposes, such as purified water or water for injection.

According to the invention, the pH value of the compositions is not particularly limited, and preferably selected to ensure that the compositions can be used as injection products, particularly intravenous injection products.

Preferably, the compositions are injection products, such as meloxicam intravenous injection products.

According to the embodiments of the invention, the pH of the compositions can be in the range of 3.0 to 10.0, preferably 6.5 to 10.0, such as 6.8 to 9.0, or 7.2 to 9.0, particularly 7.4 to 9.0.

Alternatively, the compositions can also contain pH regulators.

According to the embodiments of the invention, the pH regulator can be selected from an alkaline pH regulator and/or an acidic pH regulator, for example, those reagent that is used as a pH regulator suitable for injections or intravenous injections.

According to the embodiments of the invention, the alkaline pH regulator can be one, two or more selected from the group consisting of sodium hydroxide, sodium carbonate, sodium bicarbonate, triethylamine, diethanolamine, sodium phosphate, disodium hydrogen phosphate, sodium dihydrogen phosphate, Tris (tri(hydroxymethyl)aminomethane), arginine, lysine, histidine and glycine; preferably, the alkaline pH regulator is one, two or more selected from the group consisting of sodium hydroxide, sodium carbonate, sodium bicarbonate, disodium hydrogen phosphate, sodium dihydrogen phosphate, sodium phosphate, Tris, arginine, lysine, glycine and triethylamine; more preferably, the alkaline pH regulator is selected from the group consisting of sodium hydroxide, sodium carbonate, sodium phosphate, Tris or lysine; for example, the alkaline pH regulator is selected from sodium hydroxide or lysine.

According to the embodiments of the invention, the acidic pH regulator can be one, two or more selected from the group consisting of vitamin C (also known as ascorbic acid), lactic acid, malic acid, fumaric acid, citric acid, tartaric acid, succinic acid, hydrochloric acid, phosphoric acid and acetic acid; preferably, the acidic pH regulator is one, two or more selected from the group consisting of lactic acid, malic acid, tartaric acid, citric acid, hydrochloric acid, phosphoric acid and acetic acid.

According to the embodiments of the invention, the ratios of the mass of meloxicam to the volume of the cosolvents can be 5 to 35 mg/mL, such as 7 to 32 mg/mL, or 10-30 mg/mL, 15-30 mg/mL, or 20-25 mg/mL, etc.

According to the embodiments of the invention, the meloxicam compositions contain meloxicam, cosolvents and pH regulators;
  wherein the cosolvents are mixed solvents containing water and organic solvents, in which the organic solvent is one, two or more selected from the group consisting of ethanol, propylene glycol, polyethylene glycol 300, and polyethylene glycol 400, preferably polyethylene glycol 300 and/or polyethylene glycol 400;
  the volume concentration of the organic solvents in the cosolvents are in the range of 5% to 80%, such as 10% to 60%, or 15% to 50%, such as 20% to 40%, for example, 15%, 18%, 19%, 20%, 25% or 30%;
  the pH regulator is selected from a alkaline pH regulator and/or an acidic pH regulator, in which the alkaline pH regulator is selected from the group consisting of sodium hydroxide, sodium carbonate, sodium phosphate, Tris or lysine, preferably sodium hydroxide or lysine; the acidic pH regulator is one, two or more selected from the group consisting of lactic acid, malic acid, tartaric acid, citric acid, hydrochloric acid, phosphoric acid and acetic acid;

The ratio of the mass of meloxicam to the volume of the cosolvents can be 5 to 35 mg/mL, such as 7 to 32 mg/mL, or 10-30 mg/mL, or 15-30 mg/mL, or 20-25 mg/mL, etc.

In the meloxicam compositions provided in the invention, the amount of meloxicam is not particularly limited, for example, it may be up to 10 g or more, 50 g or more, 100 g or more, 200 g or more, or 300 g or more, and the specific amount thereof can be determined depending on the scale of production.

In the meloxicam compositions provided in the invention, the amount of the cosolvents is not particularly limited, for example, up to 1 L or more, 5 L or more, 10 L or more, 15 L or more, or 20 L or more, and the specific amount thereof can be determined depending on the scale of production.

Preferably, meloxicam is dissolved in the cosolvents.

According to the embodiments of the invention, the liquid meloxicam compositions preferably contain no solubilizer and/or no surfactant; preferably, the compositions contain no solubilizer and no surfactant. Wherein, the solubilizer includes, but is not limited to, a solubilizer used in a pharmaceutical preparation, for example, selected from a solubilizer known to be used for injections, such as cyclodextrin and its derivatives. As an example, the cyclodextrin includes α-cyclodextrin, β-cyclodextrin or γ-cyclodextrin, and the derivatives include, but are not limited to, one, two or more of an ether derivative, an ester derivative, polymer, etc. of α-cyclodextrin, of β-cyclodextrin, of γ-cyclodextrin; such as, the ether derivative is selected from one, two or more of a glucose derivative, a hydroxypropyl derivative, a methyl derivative, etc.; exemplarily, the derivative is selected from one, two or more of hydroxyethyl-β-cyclodextrin, hydroxypropyl-β-cyclodextrin, sulfobutyl-β-cyclodextrin, etc.; wherein, the surfactant includes, but are not limited to, a surfactant known to be used for pharmaceutical preparations or compositions, for example, selected from a surfactant used for injections, such as one, two or more selected from the group consisting of polysorbate 80, a polyoxyethylene castor oil derivative, poloxamer, polyethylene glycol 15-hydroxystearate, etc.

The invention also provides a method for preparing the meloxicam compositions, including mixing meloxicam, water, organic solvents, and optionally pH regulators, wherein the organic solvents are as defined above.

According to some embodiments of the invention, the preparation method includes mixing meloxicam and a cosolvent, wherein the cosolvent is a mixed solvent containing water and an organic solvent.

According to the invention, the preparation method can further include a step for providing the cosolvent, for example, mixing water and the cosolvent.

When the composition contains a pH regulator, the preparation method also includes mixing water and the first pH regulator, and then further mixing with an organic solvent to obtain a mixed solution; or firstly mixing water and an organic solvent, and then further mixing with the pH regulator to obtain a mixed solution.

Preferably, the method of preparation also further includes mixing the mixed solution and meloxicam to give a mixed solution containing meloxicam.

Preferably, the preparation method also includes mixing the mixed solution containing meloxicam and the second pH regulator, wherein the first and the second pH regulators are the same or different, and are each independently selected from the above-defined pH regulators. Preferably, the first pH regulator is an alkaline regulator, and the second pH regulator is an acidic regulator.

In other embodiments of the invention, the preparation method may include mixing an alkaline aqueous solution containing meloxicam with an organic solvent.

Preferably, the preparation method also includes providing an alkaline aqueous solution containing meloxicam by firstly mixing the first pH regulator and water, and then mixing with meloxicam to obtain an alkaline aqueous solution containing meloxicam.

Preferably, the preparation method also includes mixing the alkaline aqueous solution containing meloxicam and an organic solvent to obtain a mixed solution containing meloxicam, and then mixing with the second pH regulator, wherein the first and the second pH regulators are the same or different, and are each independently selected from the above-defined pH regulators.

According to the embodiments of the invention, the preparation method can include the following steps:
1) mixing a pH regulator and water so that the pH of water is ≥10.0, for example, pH≥11.0, or pH≥12.0, or pH≥12.5, or pH≥13.0, to obtain an alkaline aqueous solution;
2) mixing an organic solvent and the alkaline aqueous solution obtained in step 1) to obtain a mixed solution;
3) adding meloxicam into the mixed solution obtained in step 2) to obtain a mixed solution containing meloxicam;
4) adjusting the pH of the solution obtained in step 3) to obtain a meloxicam composition.

Alternatively, according to the embodiments of the invention, the preparation method can include the following steps:
1) mixing a pH regulator and water so that the pH of water is ≥10.0, for example, pH≥11.0, or pH≥12.0, or pH≥12.5, or pH≥13.0, to obtain an alkaline aqueous solution;
2) mixing meloxicam and the alkaline aqueous solution obtained in step 1) to obtain an alkaline aqueous solution containing meloxicam;
3) adding an organic solvent into the mixed solution obtained in step 2) to obtain a mixed solution containing meloxicam;
4) adjusting the pH of the solution obtained in step 3) to obtain a meloxicam composition.

Generally, the temperature in the preparation method is not particularly limited. For example, the temperature in step 1), 2), 3) or 4) can be in the range of 5° C. to 80° C., and these temperatures can be adjusted in accordance with specific conditions according to the invention. According to the exemplary preparation method of the invention, without waiting for the above-mentioned alkaline aqueous solution to cool, an organic solvent may be added under stirring. Preferably, the temperatures in step 1), 2), 3) or 4) are in the range of 10° C. to 60° C., more preferably 20° C. to 60° C.; as an example, the temperature can be 20° C., 25° C., 30° C., 40° C., 50° C. or 60° C.

According to the embodiments of the invention, the stirring in each step such as step 1), 2), 3) or 4) may promote mixing, and the stirring time can be 10 minutes or more, for example, 20 minutes, 30 minutes, 40 minutes, 50 minutes, 60 minutes or more in the above different embodiments.

The invention also provides a liquid preparation, such as an injection, preferably an intravenous injection, the injection containing the above-mentioned meloxicam compositions.

According to the invention, the injection can also include a container, such as an ampoule, a vial or a multi-dose container, containing the above-mentioned meloxicam composition.

According to the invention, the injection may include a small-volume injection (20 mL or less, such as 1 mL, 2 mL, 3 mL, 4 mL, 5 mL, 6 mL, 7 mL, 8 mL, 9 mL, 10 mL, 15 mL, or 20 mL) and a large-volume injection (50 mL or more, such as 50 mL, 60 mL, 70 mL, 75 mL, 80 mL, 90 mL, 100 mL, 250 mL, 500 mL, etc.).

The invention also provides a method for preparing the injection, including placing the meloxicam composition in a container; preferably, the composition is also sterilized before or after being placed in the container. The sterilization may be moist heat sterilization or sterilization by filtration.

The invention also provides the use of the above-mentioned meloxicam compositions in the treatment of diseases (such as post-operative analgesia, rheumatoid arthritis, painful osteoarthritis, ankylosing spondylitis).

The invention also provides the use of the above-mentioned meloxicam compositions in the preparation of drugs, especially for the treatment of post-operative analgesia, rheumatoid arthritis, painful osteoarthritis or ankylosing spondylitis.

Preferably, the drug is an injection product, especially an intravenous injection product.

In order to improve the above technical problems, the following technical solution is also provided in the second aspect of the invention: a meloxicam composition, the composition containing meloxicam, solvents, and pH regulators, wherein the pH regulators include at least citric acid.

According to the invention, the solvents can be selected from water, organic solvents, or cosolvents, wherein the cosolvents are mixed solvents of water and organic solvents.

According to the embodiments of the invention, the volume concentrations of the organic solvents in the cosolvents are in the range of 1% to 80%, preferably 5% to 80%, such as 10% to 60%, or 15% to 50%, or 15% to 25%, or 20% to 40%, for example, 15%, 16%, 17%, 18%, 19%, 20%, 25% or 30%.

According to the invention, the organic solvent is one, two or more selected from the group consisting of ethanol, propylene glycol, butanediol, isopropanol, tetrahydrofurfurol, tetrahydrofuran polyethylene glycol ether, glycerol, polyethylene glycol (also known as PEG, such as polyethylene glycol 300, polyethylene glycol 400, polyethylene glycol 600), etc.; preferably one, two or more selected from the group consisting of ethanol, propylene glycol, butanediol, tetrahydrofurfurol, glycerol, polyethylene glycol 300, polyethylene glycol 400; such as one, two or more selected from the group consisting of ethanol, propylene glycol, polyethylene glycol 300, polyethylene glycol 400; exemplarily, the organic solvent is selected from polyethylene glycol 300 and/or polyethylene glycol 400.

According to the invention, water in the cosolvents can be that suitable for pharmaceutical purposes, such as purified water and water for injection.

According to the invention, the pH values of the compositions are not particularly limited, and preferably selected to ensure that the compositions can be used for injections, particularly intravenous injections.

Preferably, the compositions are injection products, such as meloxicam intravenous injection products.

According to the embodiments of the invention, the pH of the compositions can be in the range of 3.0 to 10.0, preferably 6.5 to 10.0, such as 6.8 to 9.0, or 7.2 to 9.0, or 7.4 to 9.0, particularly, 7.5, 7.6, 7.7, 7.8, 7.9, 8.0, 8.1, 8.2, 8.3, 8.4, 8.5, 8.6, 8.7, 8.8 or 8.9.

According to the embodiment of the invention, the pH regulator is selected from an acidic pH regulator or a combination of an acidic pH regulator and an alkaline pH regulator, provided that the acidic pH regulator contains at least citric acid.

According to the embodiments of the invention, the acidic pH regulator can be selected from citric acid, or a mixture of citric acid and one, two or more acids selected from the group consisting of Vitamin C (also known as ascorbic acid), lactic acid, malic acid, fumaric acid, citric acid, tartaric acid, succinic acid, hydrochloric acid, phosphoric acid and acetic acid.

According to the embodiments of the invention, the alkaline pH regulator can be one, two or more selected from the group consisting of sodium hydroxide, sodium carbonate, sodium bicarbonate, triethylamine, diethanolamine, sodium phosphate, disodium hydrogen phosphate, sodium dihydrogen phosphate, Tris (tri(hydroxymethyl)aminomethane), meglumine, arginine, lysine, histidine and glycine; preferably, the alkaline pH regulator is one, two or more selected from the group consisting of sodium hydroxide, sodium carbonate, sodium bicarbonate, disodium hydrogen phosphate, sodium dihydrogen phosphate, sodium phosphate, Tris, meglumine, arginine, lysine, glycine and triethylamine; more preferably, the alkaline pH regulator is selected from the group consisting of sodium hydroxide, sodium carbonate, sodium phosphate, Tris or lysine; exemplarily, the alkaline pH regulator is selected from sodium hydroxide or lysine.

In an exemplary technical solution of the invention, the pH regulator includes sodium hydroxide and/or meglumine, and citric acid; or, the pH regulator consists of sodium hydroxide and citric acid, or consists of meglumine and citric acid.

According to the embodiments of the invention, the ratios of the mass of meloxicam to the volume of the cosolvents can be 5 to 35 mg/mL, such as 7 to 32 mg/mL, for example, 10-30 mg/mL, 15-30 mg/mL, 20-25 mg/mL, etc.

Preferably, meloxicam is dissolved in the cosolvents.

According to the embodiments of the invention, the liquid meloxicam compositions preferably contain no solubilizer and/or no surfactant; preferably, the compositions contain no solubilizer and no surfactant. Wherein, the solubilizer includes, but is not limited to, a solubilizer used in a pharmaceutical preparation, for example, selected from a solubilizer known to be used for injections, such as cyclodextrin and its derivatives. As an example, the cyclodextrin includes α-cyclodextrin, β-cyclodextrin or γ-cyclodextrin, and the derivatives include, but are not limited to, one, two or more of an ether derivative, an ester derivative, polymer, etc. of α-cyclodextrin, of β-cyclodextrin, or of γ-cyclodextrin; such as, the ether derivative is selected from one, two or more of a glucose derivative, a hydroxypropyl derivative, a methyl derivative, etc.; exemplarily, the derivative is selected from one, two or more of hydroxyethyl-β-cyclodextrin, hydroxypropyl-β-cyclodextrin, sulfobutyl-β-cyclodextrin, etc.; wherein, the surfactant includes, but are not limited to, a surfactant known to be used for pharmaceutical preparations or compositions, for example, selected from a surfactant used for injections, such as one, two or more selected from the group consisting of polysorbate 80, a polyoxyethylene castor oil derivative, poloxamer, polyethylene glycol 15-hydroxystearate, etc.

The invention also provides a method for preparing the meloxicam composition, including mixing meloxicam, a solvent (such as water and/or an organic solvent), and a pH regulator, wherein the solvent and the pH regulator are as defined above.

According to some embodiments of the invention, the preparation method includes mixing meloxicam and a cosolvent, wherein the cosolvent is a mixed solvent containing water and an organic solvent.

According to the invention, the preparation method can further include the steps for providing the cosolvent, for example, mixing water and the cosolvent.

When the composition contains a pH regulator, the preparation method also includes firstly mixing water and the first pH regulator, and then further mixing with an organic solvent to obtain a mixed solution; or firstly mixing water and an organic solvent, and then further mixing with the second pH regulator to obtain a mixed solution.

Preferably, the preparation method also further includes mixing the mixed solution and meloxicam to obtain a mixed solution containing meloxicam.

Preferably, the preparation method also includes mixing the mixed solution containing meloxicam and the second pH regulator.

In other embodiments of the invention, the preparation method can include mixing an alkaline aqueous solution containing meloxicam and an organic solvent.

Preferably, the preparation method also includes providing an alkaline aqueous solution containing meloxicam, for example, firstly mixing the first pH regulator and water, and then mixing with meloxicam to obtain an alkaline aqueous solution containing meloxicam.

Preferably, the preparation method also includes mixing the alkaline aqueous solution containing meloxicam and an organic solvent to obtain a mixed solution containing meloxicam, and then mixing with the second pH regulator.

According to the invention, the first and the second pH regulators are the same or different, and are each independently selected from the above-defined pH regulators, provided that the second pH regulator is an acidic pH regulator containing citric acid. Preferably, the first pH regulator is an alkaline pH regulator, and the second pH regulator is an acidic pH regulator containing citric acid.

According to the embodiments of the invention, the preparation method can include the following steps:
1) mixing the first pH regulator and water so that the pH of water is ≥10.0, for example, pH≥11.0, or pH≥12.0, or pH≥12.5, or pH≥13.0, to obtain an alkaline aqueous solution;
2) mixing an organic solvent and the alkaline aqueous solution obtained in step 1) to obtain a mixed solution;
3) adding meloxicam into the mixed solution obtained in step 2) to obtain a mixed solution containing meloxicam;
4) adjusting the pH of the solution obtained in step 3) by using the second pH regulator to obtain a meloxicam composition.

Alternatively, according to the embodiments of the invention, the preparation method may include the following steps:
1) mixing the first pH regulator and water so that the pH of water is ≥10.0, for example, pH≥11.0, or pH≥12.0, or pH≥12.5, to obtain an alkaline aqueous solution;
2) mixing meloxicam and the alkaline aqueous solution obtained in step 1) to obtain an alkaline aqueous solution containing meloxicam;
3) adding an organic solvent into the mixed solution obtained in step 2) to obtain a mixed solution containing meloxicam;
4) adjusting the pH of the solution obtained in step 3) by using the second pH regulator to obtain a meloxicam composition.

Generally, the temperature in the preparation method is not particularly limited. For example, the temperature in step 1), 2), 3) or 4) can be in the range of 5° C. to 80° C., and these temperatures can be adjusted in accordance with specific conditions according to the invention. According to the exemplary method of the preparation of the invention, without waiting for the above-mentioned alkaline aqueous solution to cool, an organic solvent may be added under stirring. Preferably, the temperature in step 1), 2), 3) or 4) is in the range of 10° C. to 60° C., more preferably 20° C. to 60° C.; as an example, the temperature can be 20° C., 25° C., 30° C., 40° C., 50° C. or 60° C.

According to the embodiments of the invention, the stirring in each step such as step 1), 2), 3) or 4) can promote mixing, and the mixing time can be 10 minutes or more, for example, 20 minutes, 30 minutes, 40 minutes, 50 minutes, 60 minutes or more in the above different embodiments.

The invention also provides a liquid pharmaceutical preparation, such as an injection, preferably an intravenous injection, and the injection containing the above-mentioned meloxicam compositions.

According to the invention, the injection can also include a container, such as an ampoule, a vial or a multi-dose container, containing the above-mentioned meloxicam composition.

According to the invention, the injection can include a small-volume injection (20 mL or less, such as 1 mL, 2 mL, 3 mL, 4 mL, 5 mL, 6 mL, 7 mL, 8 mL, 9 mL, 10 mL, 15 mL, or 20 mL) and a large-volume injection (50 mL or more, such as 50 mL, 60 mL, 70 mL, 75 mL, 80 mL, 90 mL, 100 mL, 250 mL, 500 mL, etc.).

The invention also provides a method for preparing the injection, including placing a meloxicam composition in a container; preferably, the composition is also sterilized before or after being placed in the container. The sterilization can be moist heat sterilization or sterilization by filtration.

The invention also provides the use of the above-mentioned meloxicam compositions in the treatment of diseases (such as post-operative analgesia, rheumatoid arthritis, painful osteoarthritis, or ankylosing spondylitis).

The invention also provides the use of the above-mentioned meloxicam compositions in the preparation of drugs, especially for the treatment of post-operative analgesia, rheumatoid arthritis, painful osteoarthritis or ankylosing spondylitis.

Preferably, the drug is an injection product, particularly an intravenous injection product.

The beneficial effects of the invention include:

It is surprisingly found in the invention that the pharmaceutical compositions provided in the first aspect of the invention can significantly increase the solubility of meloxicam in liquid preparations. For example, when the pH of the solution systems is adjusted to 12.0 or more before the dissolution of meloxicam, and the organic solvents in the cosolvents are ≥5% by volume, the concentrations of meloxicam may reach 10 mg/mL or even higher, which indicates that the solubility of the drug is greatly improved.

Meanwhile, it is also surprisingly found in the invention that the compositions of the invention exhibit excellent stability. For example, when the organic solvents are in the same proportion in the cosolvents, and polyethylene glycol (such as PEG 300 or PEG 400, etc.) is used as one of the components in the cosolvents, the stability is significantly improved. No precipitation occurs during long-term storage, thereby effectively reducing the content of impurities such as degradation products, and stable liquid compositions are obtained under injection conditions (especially under intravenous injection conditions). In other words, the cosolvents selected in the invention can dramatically increase the solubility of the drug, and also significantly enhance the stability of the drug.

Since excipients, such as solubilizers, surfactants, etc., are not contained in the compositions of the invention, the irritability of the compositions tends to decrease and the safety is better. The meloxicam compositions of the invention can even be directly used for intravenous injection bolus, and the effective therapeutic concentrations for postoperative analgesia are quickly reached.

Furthermore, the preparation technique of the compositions is simple and it can be completed by stirring and dispersing in a short time at room temperature, and the large-scale production is easy to be achieved.

It is also surprisingly found in the invention that the stability of the compositions provided in the second aspect of the invention is significantly improved. In particular, when citric acid is used as an acidic pH regulator, the content of degradation product B is effectively reduced, thus dramatically improving the safety of the liquid preparations, and no precipitation occurs during long-term storage.

Meanwhile, the solubility of meloxicam in the compositions of the invention is significantly increased, and the concentrations of meloxicam can reach 10 mg/mL or even higher. It is very beneficial to the use of meloxicam as an injection (especially as an intravenous injection).

Furthermore, the preparation technique of the compositions is simple and it can be completed by stirring and dispersing in a short time at room temperature, and the large-scale production is easy to be achieved.

EXAMPLES

The invention will be further described in more detail below in conjunction with specific examples. The following examples are merely illustrative of the invention and are not to be construed as limiting the scope of the invention. Any technology that is implemented based on the above-described contents of the invention is encompassed within the scope of the invention.

Unless otherwise specified, the active pharmaceutical ingredients and reagents used in the following examples are all commercially available, or can be prepared by known methods.

Wherein, the meloxicam content is 99.9% and the content of total impurities is 0.03% in raw materials in Examples A1 to A15 and Comparative Examples A1 to A5.

The method for determining the meloxicam content described in the examples and comparative examples of the invention refers to the method in USP40-NF35 Monographs: Method for determination of meloxicam content.

Example A1 Meloxicam Composition

| Formulation: Meloxicam | 1.0 g |
| PEG 400 | 15 mL |
| Water | added to 100 mL |
| Sodium hydroxide/phosphoric acid (pH regulator) | appropriate amount |

Preparation method: formulating a sodium hydroxide solution with a pH of 12.0, adding a formulation amount of PEG 400, stirring the mixture to be homogenous at room temperature, then adding meloxicam, stirring to dissolve meloxicam, and adjusting the pH of the solution to 7.8 with phosphoric acid to obtain the meloxicam composition. No insoluble particles/visible foreign matter occurred at room temperature. No insoluble particles/visible foreign matter occurred at 2-8° C. for 15 days.

Example A2 Meloxicam Composition

| Formulation: Meloxicam | 1.0 g |
| PEG 400 | 15 mL |
| Water | added to 100 mL |
| Sodium hydroxide/phosphoric acid (pH regulator) | appropriate amount |

Preparation method: formulating a sodium hydroxide solution with a pH of 12.0, adding meloxicam, stirring the mixture to dissolve meloxicam at room temperature, then adding a formulation amount of PEG 400, stirring the mixture to be homogenous, and adjusting the pH of the solution to 7.4 with phosphoric acid to obtain the meloxicam composition. No insoluble particles/visible foreign matter occurred at room temperature. No insoluble particles/visible foreign matter occurred at 2-8° C. for 15 days.

Example A3 Meloxicam Composition

| Formulation: Meloxicam | 1.0 g |
| PEG 300 | 15 mL |
| Water | added to 100 mL |
| Sodium hydroxide/phosphoric acid (pH regulator) | appropriate amount |

Preparation method: formulating a sodium hydroxide solution with a pH of 12.0, adding a formulation amount of PEG 300, stirring the mixture to be homogenous, then adding meloxicam, stirring to dissolve meloxicam, and adjusting the pH of the solution to 8.0 with phosphoric acid to obtain the meloxicam composition. No insoluble particles/visible foreign matter occurred at room temperature. No insoluble particles/visible foreign matter occurred at 2-8° C. for 15 days.

Example A4 Meloxicam Composition

| Formulation: Meloxicam | 1.0 g |
| PEG 400 | 15 mL |
| Water | added to 100 mL |
| Sodium hydroxide/phosphoric acid (pH regulator) | appropriate amount |

Preparation method: formulating a sodium hydroxide solution with a pH of 12.0, adding a formulation amount of PEG 400, stirring the mixture to be homogenous, then adding meloxicam, stirring the mixture to dissolve the meloxicam, and adjusting the pH of the solution to 8.2 with phosphoric acid to obtain the meloxicam composition. No insoluble particles/visible foreign matter occurred at room temperature. No insoluble particles/visible foreign matter occurred at 2-8° C. for 15 days.

Example A5 Meloxicam Composition

| | |
|---|---|
| Formulation: Meloxicam | 0.938 g |
| PEG 400 | 10 mL |
| Water | added to 50 mL |
| Sodium hydroxide/lactic acid (pH regulator) | appropriate amount |

Preparation method: formulating a sodium hydroxide solution with a pH of 12.0, adding a formulation amount of PEG 400, stirring the mixture to be homogenous, then adding meloxicam, stirring to dissolve meloxicam, and adjusting the pH of the solution to 7.8 with lactic acid to obtain the meloxicam composition. No insoluble particles/visible foreign matter occurred at room temperature. No insoluble particles/visible foreign matter occurred at 2-8° C. for 15 days.

Example A6 Meloxicam Composition

| | |
|---|---|
| Formulation: Meloxicam | 0.938 g |
| PEG 400 | 10 mL |
| Water | added to 50 mL |
| Sodium hydroxide/malic acid (pH regulator) | appropriate amount |

Preparation method: formulating a sodium hydroxide solution with a pH of 12.0, adding a formulation amount of PEG 400, stirring the mixture to be homogenous, then adding meloxicam, stirring to dissolve meloxicam, and adjusting the pH of the solution to 8.4 with malic acid to obtain the meloxicam composition. No insoluble particles/visible foreign matter occurred at room temperature. No insoluble particles/visible foreign matter occurred at 2-8° C. for 15 days.

Example A7 Meloxicam Composition

| | |
|---|---|
| Formulation: Meloxicam | 0.938 g |
| PEG 400 | 10 mL |
| Water | added to 50 mL |
| Sodium hydroxide/ tartaric acid (pH regulator) | appropriate amount |

Preparation method: formulating a sodium hydroxide solution with a pH of 12.0, adding a formulation amount of PEG 400, stirring the mixture to be homogenous, then adding meloxicam, stirring to dissolve meloxicam, and adjusting the pH of the solution to 8.2 with tartaric acid to obtain a meloxicam composition. No insoluble particles/visible foreign matter occurred at room temperature. No insoluble particles/visible foreign matter occurred at 2-8° C. for 15 days.

Example A8 Meloxicam Composition

| | |
|---|---|
| Formulation: Meloxicam | 1.0 g |
| Propylene glycol | 15 mL |
| Water | added to 100 mL |
| Sodium hydroxide/ phosphoric acid (pH regulator) | appropriate amount |

Preparation method: formulating a sodium hydroxide solution with a pH of 12.0, adding a formulation amount of propylene glycol, stirring the mixture to be homogenous, then adding meloxicam, stirring to dissolve meloxicam, and adjusting the pH of the solution to 8.4 with phosphoric acid to obtain the meloxicam composition. No insoluble particles/visible foreign matter occurred at room temperature. A small number of insoluble particles occurred at 2-8° C. for 15 days.

Example A9 Meloxicam Composition

| | |
|---|---|
| Formulation: Meloxicam | 1.0 g |
| Glycerol | 15 mL |
| Water | added to 100 mL |
| Sodium hydroxide/ phosphoric acid (pH regulator) | appropriate amount |

Preparation method: formulating a sodium hydroxide solution with a pH of 12.0, adding a formulation amount of glycerol, stirring the mixture to be homogenous, then adding meloxicam, stirring to dissolve meloxicam, and adjusting the pH of the solution to 8.6 with phosphoric acid to obtain the meloxicam composition. No insoluble particles/visible foreign matter occurred at room temperature. A small amount of insoluble particles occurred at 2-8° C. for 15 days.

Example A10 Meloxicam Composition

| | |
|---|---|
| Formulation: Meloxicam | 1.0 g |
| Butanediol | 15 mL |
| Water | added to 100 mL |
| Sodium hydroxide/ phosphoric acid (pH regulator) | appropriate amount |

Preparation method: formulating a sodium hydroxide solution with a pH of 12.0, adding a formulation amount of butanediol, stirring the mixture to be homogenous, then adding meloxicam, stirring to dissolve meloxicam, and adjusting the pH of the solution to 8.2 with phosphoric acid to obtain a meloxicam composition. No insoluble particles/visible foreign matter occurred at room temperature. A small amount of insoluble particles occurred at 2-8° C. for 15 days.

Example A11 Meloxicam Composition

| | |
|---|---|
| Formulation: Meloxicam | 1.0 g or 1.5 g |
| PEG 400 | 15 mL |
| Sodium hydroxide/ citric acid (pH regulator) | appropriate amount |
| Water | added to 100 mL |

Preparation method: formulating a sodium hydroxide solution with a pH of 12.0, adding a formulation amount of PEG 400, stirring the mixture to be homogenous, then adding meloxicam, stirring to dissolve meloxicam, and adjusting the pH of the solution to 7.8, 8.0, 8.2, 8.4, 8.6, 8.8 or 9.0, respectively, with citric acid to obtain the meloxicam composition. No insoluble particles/visible foreign matter occurred at room temperature. No insoluble particles/visible foreign matter occurred at 2-8° C. for 15 days.

Example A12 Up-Scaling Preparation of the Meloxicam Compositions of the Invention According to formulas F1 to F14 shown in the table below, 250 mL of liquid compositions with different components were prepared. Meloxicam compositions were obtained by formulating aqueous sodium hydroxide solutions with a pH of 13.0, adding a formulation amounts of organic solvents, stirring the mixtures to be homogenous, adding meloxicam, stirring to dissolve meloxicam, and adjusting the pH of the solutions to the corresponding values with phosphoric acid.

TABLE A1

Formulas of meloxicam liquid compositions

| Sample | MLX (g) | PEG 400 (mL) | PEG 300 (mL) | Propylene glycol (mL) | Purified water (mL) | Measured pH of a solution |
|---|---|---|---|---|---|---|
| F1 | 1.878 | 25 | / | / | 225 | 7.45 |
| F2 | 1.877 | 50 | / | / | 200 | 6.80 |
| F3 | 1.876 | 75 | / | / | 175 | 7.52 |
| F4 | 4.691 | 50 | / | / | 200 | 7.52 |
| F5 | 7.499 | 50 | / | / | 200 | 8.20 |
| F6 | 1.873 | 50 | / | / | 200 | 8.22 |
| F7 | 4.703 | 75 | / | / | 175 | 6.82 |
| F8 | 4.699 | 25 | / | / | 225 | 8.16 |
| F9 | 4.692 | 50 | / | / | 200 | 7.53 |
| F10 | 4.673 | 75 | / | / | 175 | 8.22 |
| F11 | 4.676 | / | 25 | / | 225 | 8.21 |
| F12 | 7.508 | / | 50 | / | 200 | 8.50 |
| F13 | 1.882 | / | / | 50 | 200 | 8.20 |
| F14 | 4.686 | / | / | 75 | 175 | 7.79 |

Example A13 Stability Testing of Meloxicam Compositions

Each of the sample solutions of F1-F14 in Example A12 was sampled, filtered through 0.22 μm microporous filter membranes, and 5 mL of each filtrate was taken into 10 ml vials and the vials were sealed with caps. The vials were placed at room temperature, at 2-8° C. in the refrigerator, and at 60° C. in a constant temperature and humidity incubator, respectively, to investigate crystallization and changes of related substances. The results are shown in the table below.

TABLE A2

Stability testing of meloxicam compositions

| | Stability (30 days) | | | |
|---|---|---|---|---|
| Sample | Insoluble particles/visible foreign matter at room temperature | Insoluble particles/visible foreign matter at 2-8° C. | Degradation product B content at 60° C. (%) | Degradation product B content at 25° C. (%) |
| F1 | No | No | 0.73 | 0.02 |
| F2 | No | No | 0.67 | 0.01 |
| F3 | No | No | 0.30 | 0.01 |
| F4 | No | No | 0.40 | 0.01 |
| F5 | No | No | 0.39 | 0.01 |
| F6 | No | No | 0.29 | 0 |
| F7 | No | No | 0.41 | 0.01 |
| F8 | No | No | 1.07 | 0.01 |
| F9 | No | No | 0.40 | 0.01 |
| F10 | No | No | 0.21 | 0.01 |
| F11 | No | No | no sample | no sample |
| F12 | No | No | 0.25 | no sample |
| F13 | No | occurring a small amount of crystals | no sample | no sample |
| F14 | No | occurring a small amount of crystals | no sample | no sample |

Example A14 Up-Scaling Preparation of the Meloxicam Compositions of the Invention Various liquid compositions with different formulas were prepared according to the formulas given in table A3. Aqueous sodium hydroxide solutions with a pH of 13.0 were prepared. The formulation amount of organic solvents was added. The mixtures were stirred to be homogenous. Different batches of meloxicam were added and dissolved with stirring. The pH of the solutions was adjusted to the corresponding pH with phosphoric acid. The solutions were sterilized to obtain meloxicam compositions.

TABLE A3

Formulas of meloxicam liquid compositions

| Sample | MLX (g) | PEG 400 (L) | Purified water (L) | Measured pH of the solution |
|---|---|---|---|---|
| S1 | 10.0 | 0.2 | 0.800 | 8.6 |
| S2 | 15.0 | 0.2 | 0.800 | 8.8 |
| S3 | 300 | 3.54 | 15.62 | 8.55 |

Among them, S1 and S2 are samples from the same batch and S3 are another batch of sample.

Example A15 Stability Testing of Meloxicam Compositions

The stability of the samples in Example A14 were investigated in long-term and accelerated conditions, and the results are shown in the table below.

Long-term stability testing: according to the guidelines on stability testing of drug substances and drug products in Chinese Pharmacopoeia 2015 edition, volume IV 9001, the long-term stability of samples S1 and S2 in Example A14 were investigated at a temperature of 30° C.±2° C., RH 65%±5%, for 3, 6, 9 and 12 months.

Accelerated stability testing: according to the guidelines on stability testing of drug substances and drug products in Chinese Pharmacopoeia 2015 edition, volume IV 9001, the accelerated stability of the samples S1, S2 and S3 in Example A14 were investigated at a temperature of 40° C.±2° C., RH 75%±5%, for 1, 2, 3 and 6 months.

TABLE A4

Stability testing of meloxicam compositions

| Sample | | S1 | S2 | S3 |
|---|---|---|---|---|
| 0 | Content (mg/g) | 9.5 | 14.2 | 14.8 |
| | Degradation impurity (%) | 0.13 | 0.12 | 0.00 |
| | Total impurity (%) | 0.23 | 0.17 | 0.05 |
| | pH | 8.2 | 8.2 | 8.4 |
| Accelerated for 1 month (40° C.) | Content (mg/g) | 9.5 | 14.3 | 14.8 |
| | Degradation impurity (%) | 0.18 | 0.16 | 0.02 |
| | Total impurity (%) | 0.24 | 0.22 | 0.21 |
| | pH | 8.5 | 8.5 | 8.5 |
| Accelerated for 2 months (40° C.) | Content (mg/g) | / | / | 14.8 |
| | Degradation impurity (%) | / | / | 0.03 |
| | Total impurity (%) | / | / | 0.18 |
| | pH | / | / | 8.7 |
| Accelerated for 3 months (40° C.) | Content (mg/g) | 9.5 | 14.2 | 14.9 |
| | Degradation impurity (%) | 0.21 | 0.19 | 0.06 |
| | Total impurity (%) | 0.33 | 0.31 | 0.21 |
| | pH | 8.7 | 8.7 | 8.5 |
| Long-term stability testing for 3 months (30° C.) | Content (mg/g) | 9.5 | 14.3 | 14.8 |
| | Degradation impurity (%) | 0.14 | 0.14 | 0.02 |
| | Total impurity (%) | 0.25 | 0.25 | 0.07 |
| | pH | 8.6 | 8.7 | 8.8 |
| Accelerated for 6 months (40° C.) | Content (mg/g) | 9.3 | 14.3 | / |
| | Degradation impurity (%) | 0.31 | 0.28 | / |
| | Total impurity (%) | 0.55 | 0.47 | / |
| | pH | 8.6 | 8.7 | / |
| Long-term stability testing for 6 months (30° C.) | Content (mg/g) | 9.5 | 14.3 | / |
| | Degradation impurity (%) | 0.21 | 0.19 | / |
| | Total impurity (%) | 0.38 | 0.34 | / |
| | pH | 8.7 | 9.0 | / |
| Long-term stability testing for 9 months (30° C.) | Content (mg/g) | 9.4 | 14.3 | / |
| | Degradation impurity (%) | 0.22 | 0.20 | / |
| | Total impurity (%) | 0.33 | 0.30 | / |
| | pH | 8.8 | 9.0 | / |
| Long-term stability testing for 12 months (30° C.) | Content (mg/g) | 9.7 | 14.6 | / |
| | Degradation impurity (%) | 0.23 | 0.23 | / |
| | Total impurity (%) | 0.69 | 0.69 | / |
| | pH | 8.7 | 8.3 | / |

Note:
The 0-day test data was obtained immediately after sample preparation was completed.

The above testing results showed that the degradation impurities and total impurities could still be kept at low levels during long-term and accelerated stability testing of the meloxicam compositions prepared on a larger scale in Example A14, indicating that the meloxicam compositions exhibited excellent stability.

Comparative Example A1 Meloxicam Liquid Composition

| Formulation: Meloxicam | 0.938 g |
|---|---|
| lysine | 0.730 g |
| PEG 400 | 10 mL |
| Water | added to 50 mL |
| phosphoric acid (pH regulator) | appropriate amount |

Preparation method: dissolving lysine and PEG 400 in water, stirring the mixture to be homogenous, adding meloxicam, stirring to dissolve meloxicam at 40° C., and adjusting the pH of the solution to 7.5 with phosphoric acid to obtain the meloxicam composition. No insoluble particles/visible foreign matter occurred at room temperature. No insoluble particles/visible foreign matter occurred at 2-8° C. for 15 days.

Comparative Example A2 Meloxicam Liquid Composition

| Formulation: Meloxicam | 0.938 g |
|---|---|
| meglumine | 0.975 g |
| PEG 400 | 10 mL |
| Water | added to 50 mL |
| phosphoric acid (pH regulator) | appropriate amount |

Preparation method: dissolving meglumine and PEG 400 in water, stirring the mixture to be homogenous, adding meloxicam, stirring for a long time above 40° C. to dissolve meloxicam, and adjusting the pH of the solution to 7.5 with phosphoric acid to obtain the meloxicam composition. No insoluble particles/visible foreign matter occurred at room temperature. No insoluble particles/visible foreign matter occurred at 2-8° C. for 15 days.

Comparative Example A3 Meloxicam Liquid Composition

| Formulation: Meloxicam | 0.938 g |
|---|---|
| arginine | 0.870 g |
| PEG 400 | 10 mL |
| Water | added to 50 mL |
| phosphoric acid (pH regulator) | appropriate amount |

Preparation method: dissolving arginine and PEG 400 in water, stirring the mixture to be homogenous, adding meloxicam, stirring for a long time above 40° C. to dissolve meloxicam, and adjusting the pH of the solution to 7.5 with phosphoric acid to obtain the meloxicam composition. A small amount of insoluble particles occurred at 2-8° C. for 7 days.

Comparative Example A4

The solubility of meloxicam was investigated in an alkali or an alkaline amino acid solution (meglumine, Tris, arginine or lysine). The solubility is listed in the table below. The test results showed that the solubility of meloxicam in a high concentration organic base or basic amino acid could reach 10 mg/mL or more. However, it took a long time to complete the preparation (more than 6 hours) at room temperature, or meloxicam was dissolved at a higher temperature (40° C.). The preparation process was complicated. Crystals were precipitated after standing overnight at room temperature, and the solutions exhibited poor stability.

TABLE A5

Solubility of meloxicam in various concentrations of organic bases or alkaline amino acids Solubility (shaking at 25° C. for 24 h) (n = 3)

| | | | | | |
|---|---|---|---|---|---|
| Meglumine (mg/mL) | 5 | 10 | 15 | 20 | 30 |
| Solubility (mg/mL) | 8.01 | 17.83 | 24.63 | 32.03 | 44.97 |
| Tris (mg/mL) | 5 | 10 | 15 | 20 | 30 |
| Solubility (mg/mL) | 5.54 | 9.07 | 11.38 | 14.26 | 18.3 |
| Arginine (mg/mL) | 7 | 14 | 20 | 30 | 40 |
| Solubility (mg/mL) | 11.25 | 11.56 | 11.59 | 12.79 | 14.22 |
| Lysine (mg/mL) | 6 | 12 | 19 | 24 | 35 |
| Solubility (mg/mL) | 10.45 | 20.58 | 29.78 | 35.89 | 42.46 |

Comparative Example A5

The solubility of meloxicam was investigated in PEG 400 aqueous solutions with varying ratios of PEG 400 to water. The solubility is shown in the table below. The results showed that the solubility of meloxicam in pure PEG 400 was only 2.27 mg/ml, which could not meet the requirements of intravenous injection.

TABLE A6

Solubility of meloxicam in PEG 400 aqueous solutions with varying ratios of PEG 400 to water
Solubility (shaking at 25° C. for 24 h)

| PEG 400 (v/v %) | 0 | 10 | 20 | 30 | 40 | 50 | 60 | 70 | 80 | 90 | 100 |
|---|---|---|---|---|---|---|---|---|---|---|---|
| Solubility (mg/mL) | 0.020 | 0.026 | 0.033 | 0.031 | 0.046 | 0.123 | 0.213 | 0.206 | 1.097 | 2.023 | 2.274 |

The above test results showed that the compositions of the invention, which contained polyethylene glycol such as PEG 400 or PEG 300 as an organic solvent, unexpectedly significantly increased the meloxicam content in the prepared compositions. Hence, liquid formulations of meloxicam, especially intravenous injections, have better application prospects and a wider range of applications, and dramatically improve therapy efficiency and patient compliance, etc. Moreover, this effect became more pronounced when the compositions with the same meloxicam content contained higher concentration of polyethylene glycol.

Furthermore, it is surprising that the compositions of the invention also exhibited excellent stability, and not only no precipitation occurred after long standing, but also degradation products and total impurities were kept at low levels. In particular, when the proportion of an organic solvent in a cosolvent was the same, the meloxicam composition prepared with the cosolvent containing polyethylene glycol, especially PEG 400, exhibited good stability and no precipitation took place after long standing.

In Examples B1-B6 and Comparative Examples B1-B4, the meloxicam content was 99.2% and the content of total impurities was 0.06% in the raw materials.

The "freeze-thaw" method was described as follows:

Placing the samples in a refrigerator at −20° C. for two days, then taking them out, and placing them under the accelerated condition of 40° C. for two days. Each freeze-thaw experiment was repeated three times, and the result at the end of the cycles was considered.

Example B1 Meloxicam Liquid Composition

| Formulation: Meloxicam | 1 g or 1.5 g |
|---|---|
| PEG 400 | 15 mL |
| Sodium hydroxide/phosphoric acid or citric acid (pH regulator) | appropriate amount |
| Water | added to 100 mL |

Preparation method: formulating a sodium hydroxide solution with a pH of 12.0, adding a formulation amount of PEG 400, stirring the mixture to be homogenous, then adding two formulation amounts of meloxicam, stirring to dissolve meloxicam, and adjusting the pH of the solution to 7.8 with phosphoric acid or citric acid to obtain the meloxicam composition. No insoluble particles/visible foreign matter occurred at room temperature. No insoluble particles/visible foreign matter occurred at 2-8° C. for 15 days.

Example B2 Stability Testing of Meloxicam Liquid Compositions

Each of the sample solutions prepared in Example B1 was sampled, filtered through 0.22 μm microporous filter membranes, and 5 mL of each filtrate was taken into 10 mL vials and the vials were sealed with caps. The vials were placed at 60° C. in a constant temperature and humidity incubator to investigate the increase of the related substances. The results are shown in Table 1.

TABLE B1

Stability testing of meloxicam compositions

| Sample | Time (day) | Degradation product B content (%) | Total impurity content (%) |
|---|---|---|---|
| Meloxicam 15 mg/mL adjust pH with phosphoric acid | 0 | 0.01 | 0.05 |
| | 9 | 0.16 | 0.29 |
| Meloxicam 10 mg/mL adjust pH with phosphoric acid | 0 | 0.01 | 0.09 |
| | 9 | 0.23 | 0.39 |
| Meloxicam 10 mg/mL adjust pH with citric acid | 0 | 0 | 0.09 |
| | 9 | 0.07 | 0.23 |
| Meloxicam 15 mg/mL adjust pH with citric acid | 0 | Not detected | 0.06 |
| | 9 | 0.07 | 0.19 |

The above test results showed that, comparing with other pH regulators, the stability of meloxicam in the compositions containing citric acid as an acidic pH regulator was significantly improved and the formation of degradation product B was effectively reduced.

Moreover, when PEG 400 in Example B1 was replaced with other organic solvents such as ethanol, propylene glycol, butanediol, isopropanol, glycerin, PEG 300, etc., the results also showed that the contents of the degradation impurity B and total impurities in the compositions containing citric acid as a pH regulator were effectively reduced.

Example B3 Meloxicam Liquid Composition

| Formulation: Meloxicam | 1.5 g |
| --- | --- |
| PEG 400 | 20 mL |
| Sodium hydroxide/citric acid (pH regulator) | appropriate amount |
| Water | added to 100 mL |

Preparation method: formulating a sodium hydroxide solution with a pH of 12.0, adding a formulation amount of PEG 400, stirring the mixture to be homogenous, then adding meloxicam, stirring to dissolve meloxicam, and adjusting the pH of the solution to the required value (pH=8.0, 8.2, 8.4, 8.6, 8.8, 9.0) with citric acid to obtain the meloxicam compositions. No insoluble particles/visible foreign matter occurred at room temperature. No insoluble particles/visible foreign matter occurred at 2-8° C. for 15 days.

Example B4 Stability Testing of Meloxicam Liquid Compositions

Each of the sample solutions prepared in Example B3 was sampled, filtered through 0.22 μm microporous filter membranes, and 5 mL of each filtrate was taken into 10 mL vials and the vials were sealed with caps. The vials were placed at 60° C. in a constant temperature and humidity incubator for 10 days to investigate the increase of the related substances. The investigation result was that the content of degradation product B remained stable below 0.2%. It showed that in the compositions containing citric acid as a pH regulator, the content of degradation product B could be controlled in a low content range, even when the pH of the samples varied over a wide range. Therefore, the stability of meloxicam in the compositions and the safety of the preparations were significantly improved.

Example B5

With reference to the preparation method of Example B1, a meloxicam composition was prepared: 10% PEG 400 by volume, 18.75 mg/mL of meloxicam, and meglumine (instead of NaOH) and citric acid as pH regulators to adjust the pH of the composition to 8.2. No insoluble particles/visible foreign matter occurred at room temperature. No insoluble particles/visible foreign matter occurred at 2-8° C. for 15 days. After the product was freeze-thawed once, though small particles occurred at the bottom, they were dissolved rapidly after shaking.

Moreover, when the above-mentioned meglumine as a alkaline pH regulator was replaced with sodium hydroxide, sodium carbonate, sodium bicarbonate, triethylamine, diethanolamine, sodium phosphate, disodium hydrogen phosphate, sodium dihydrogen phosphate, Tris (tri(hydroxymethyl)aminomethane), arginine, lysine, histidine or glycine, etc., no insoluble particles/visible foreign matter occurred, either.

Example B6

With reference to the preparation method of Example B1, a meloxicam composition was prepared: 10% PEG 400 by volume, 18.75 mg/mL of meloxicam, and NaOH and citric acid as pH regulators to adjust the pH of the composition to 8.2. No insoluble particles/visible foreign matter occurred at room temperature. No insoluble particles/visible foreign matter occurred at 2-8° C. for 15 days. After the product was freeze-thawed once, no insoluble particles/visible foreign matter occurred.

Comparative Example B1

With reference to the preparation method of Example B1, a meloxicam composition was prepared: 10% PEG 400 by volume, 18.75 mg/mL of meloxicam, and NaOH and hydrochloric acid as pH regulators to adjust the pH of the composition to 8.2. Insoluble particles/visible foreign matter occurred in the composition at 2-8° C. for 1 days.

Comparative Example B2

With reference to the preparation method of Example B1, a meloxicam composition was prepared: 10% PEG 400 by volume, 18.75 mg/mL of meloxicam, and NaOH and acetic acid as pH regulators to adjust the pH of the composition to 8.2. Insoluble particles/visible foreign matter occurred in the composition at 2-8° C. for 1 days.

Comparative Example B3

With reference to the preparation method of Example B1, a meloxicam composition was prepared: 10% PEG 400 by volume, 18.75 mg/mL of meloxicam, and NaOH and phosphoric acid as pH regulators to adjust the pH of the composition to 8.2. Insoluble particles/visible foreign matter occurred in the composition at 2-8° C. for 6 days. After the product was freeze-thawed once, crystals occurred after standing, and were almost not dissolved after shaking.

Comparative Example B4

With reference to the preparation method of Example B1, a meloxicam composition was prepared: 10% PEG 400 by volume, 18.75 mg/mL of meloxicam, and meglumine and phosphoric acid as pH regulators to adjust the pH of the composition to 8.2. No insoluble particles/visible foreign matter occurred at room temperature. Insoluble particles/visible foreign matter occurred at 2-8° C. for 10 days. After the product was freeze-thawed once, a large amount of fine solids were precipitated after standing, and were dissolved rapidly after shaking.

The above test results showed that, comparing with other pH regulators, the stability of meloxicam in the compositions containing citric acid as an acidic pH regulator was significantly improved, the formation of impurities was effectively reduced, and the safety and efficiency of the preparations were surprisingly improved.

The embodiments of the invention are described above. However, the invention is not limited to the above embodiments. Any modification, equivalent alternative, improvement, etc., falling within the spirit and scope of the invention, are intended to be included within the scope of the invention.

The invention claimed is:

1. A meloxicam composition, consisting of meloxicam, water, and an organic solvent selected from polyethylene glycol 200, polyethylene glycol 300, polyethylene glycol 400, polyethylene glycol 600, and mixtures thereof,
   wherein water and the organic solvent form a cosolvent having a concentration of the organic solvent of 5% to 80%,
   a ratio of the mass of meloxicam to the volume of the cosolvent is 5 mg/mL to 35 mg/mL,
   a pH of the composition is in the range of 6.5 to 10.0.

2. A liquid pharmaceutical preparation, comprising the composition according to claim 1.

3. The liquid pharmaceutical preparation according to claim 2 in the form of an intravenous injection.

4. The composition according to claim 1, wherein the organic solvent is polyethylene glycol 300, polyethylene glycol 400, or polyethylene glycol 600.

5. The composition according to claim 1, wherein the pH of the composition is in the range of 6.8 to 10.0.

6. The composition according to claim 1, wherein the pH of the composition is in the range of 7.2 to 10.0.

7. The composition according to claim 1, wherein the pH of the composition is in the range of 7.2 to 9.0.

8. The composition according to claim 1, wherein the concentration of the organic solvent in the cosolvent is in the range of 10% to 60%.

9. The composition according to claim 1, wherein the concentration of the organic solvent in the cosolvent is in the range of 15% to 50%.

10. The composition according to claim 1, wherein the concentration of the organic solvent in the cosolvent is in the range of 20% to 40%.

11. The composition according to claim 1, wherein the ratio of the mass of meloxicam to the volume of the cosolvent is 10 mg/mL to 30 mg/mL.

12. The composition according to claim 1, wherein the ratio of the mass of meloxicam to the volume of the cosolvent is 15 mg/mL to 30 mg/mL.

* * * * *